(12) United States Patent
Sonoke et al.

(10) Patent No.: US 6,544,542 B1
(45) Date of Patent: Apr. 8, 2003

(54) FAT EMULSIONS FOR INHALATIONAL ADMINISTRATION

(75) Inventors: Satoru Sonoke, Kameoka (JP); Junzo Seki, Ibaraki (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 09/623,331

(22) PCT Filed: Mar. 3, 1999

(86) PCT No.: PCT/JP99/01004

§ 371 (c)(1),
(2), (4) Date: Aug. 30, 2000

(87) PCT Pub. No.: WO99/44594

PCT Pub. Date: Sep. 10, 1999

(30) Foreign Application Priority Data

Mar. 5, 1998 (JP) .............................................. 10-053159

(51) Int. Cl.[7] .......................... A61F 13/00; A61K 9/127; A61K 9/00; A61K 9/14
(52) U.S. Cl. ........................ 424/422; 424/450; 424/400; 424/489; 424/46
(58) Field of Search ................................ 424/422, 450, 424/400, 489

(56) References Cited

U.S. PATENT DOCUMENTS 5,997,904 A * 12/1999 Magdassi et al. ........... 424/489

FOREIGN PATENT DOCUMENTS

EP 267050 5/1988

* cited by examiner

*Primary Examiner*—Jose G. Dees
*Assistant Examiner*—Robert M DeWitty
(74) *Attorney, Agent, or Firm*—Eugene C. Rzucidlo

(57) ABSTRACT

The object of the present invention is to provide a pharmaceutical composition optimized for the administration of a drug, particularly a drug which is only sparingly soluble in water, by way of inhalation.

The present invention is a fat emulsion for inhalational administration, or a lyophilized composition thereof, which is an o/w fat emulsion comprising fat emulsion particles essentially composed of an oil component, an emulsifying agent and a drug as dispersed in water, characterized in that the average particle diameter of said fat emulsion particles lies within the range of 5~100 nm.

With the aid of a suitable inhaler, the inhalant of the invention readily yields a mist of aerosol particles fine enough to reach the alveolus; the inhalant is well amenable to size control of the aerosol particles.

12 Claims, 3 Drawing Sheets

FAT EMULSIONS FOR INHALATIONAL ADMINISTRATION

TECHNICAL FIELD

The present invention relates to a medical o/w fat emulsion containing a drug for inhalational administration.

BACKGROUND ART

As a technique for administering a drug to a human body, the method is known which comprises generating a finely divided mist of aerosol particles from a solution containing a drug by means of an inhaler such as a nebulizer and causing the mist to be inhaled from the nasal or oral cavity.

To carry out this method, the drug must be dissolved in water in advance but in the case of a drug which is hardly soluble in water, the drug must be solubilized with a surfactant or the like. However, even if an attempt is made to administer a medical solution prepared by such solubilization with a surfactant as an inhalant using an inhaler such as a nebulizer, it may not be easily administered by this route because such a solution may be irritating or produce a foam.

Another method known for inhalation therapy comprises dissolving a drug in a fat emulsion having a comparatively large vesicle size known as the lipid microsphere and causing it to be inhaled by means of an inhaler such as a nebulizer [e.g. JP Kokai H5-70346, JP Kokai H5-124965, JP Kokai H8-301762]. However, because such fat emulsions have a comparatively high viscosity and the diameter of emulsion vesicles is as large as 0.2~0.4 μm on the average, a finely divided aerosol mist such as one having a mass median aerodynamic diameter (MMAD) of 0.5~5 μm and as such capable of reaching the pulmonary alveolus can hardly be produced even if an inhaler such as a nebulizer is employed. An additional disadvantage of these emulsions is that because of the large emulsion vesicle size, those emulsions cannot be sterilized by filtration using a 0.22 μm membrane filter.

DISCLOSURE OF INVENTION

The object of the present invention is to provide a pharmaceutical composition optimized for the administration of a drug, particularly a drug which is only sparingly soluble in water, by way of inhalation.

The inventors of the present invention found after much research that an ultrafine o/w fat emulsion comprising a dispersion of fat emulsion particles as fine as the order of tens of nanometers is extremely suited for the inhalation of drugs and have developed the present invention.

The present invention, therefore, is directed to a fat emulsion for inhalant use in the form of an o/w fat emulsion comprising fat emulsion particles essentially composed of an oil component, an emulsifying agent and a drug as dispersed in water, the average particle diameter of said fat emulsion particles being within the range of 5~100 nm (hereinafter referred to as the inhalant of the invention), or a lyophilized composition thereof for inhalant use. The present invention further encompasses a method for administering a fat emulsion by way of inhalation, said fat emulsion being an o/w fat emulsion comprising fat emulsion particles essentially composed of an oil component, an emulsifying agent and a drug as dispersed in water and the average particle diameter of said fat emulsion particles being within the range of 5~100 nm, or a method for administering a lyophilized composition thereof by way of inhalation.

The present invention is now described in detail.

The oil component which can be used in the present invention is not particularly restricted inasmuch as it is an oil component which can be used in pharmaceutical preparations and includes but is not limited to vegetable oil, animal oil, neutral lipid (mono-, di- or tri-substituted glyceride), synthetic lipid, and sterol derivatives. To be specific, the vegetable oil includes soybean oil, cottonseed oil, rapeseedoil, sesame oil, corn oil, peanut oil, safflower oil, etc.; the animal oil includes fish oil, among others; the neutral lipid includes triolein, trilinolein, tripalmitin, tristearin, trimyristin, triarachidonin, etc.; the synthetic lipid includes azone, among others; the sterol derivative includes cholesteryl oleate, cholesteryl linoleate, cholesteryl myristate, cholesteryl palpitate, cholesteryl arachidate, and so on. These may be used each alone or in a combination of two or more species. The preferred oil component includes triglycerides and vegetable oils composed predominantly thereof. For all practical purposes, soybean oil is preferred and highly purified soybean oil (preferably with a glyceride content of 99 weight % or more) is particularly useful.

The level of said oil component in the inhalant of the invention should vary with the species of oil and other components and may typically be 0.1~30 w/v %, preferably 1~20 w/v %.

The emulsifier which can be used in the present invention is not particularly restricted inasmuch as it is pharmaceutically acceptable and may for example be a phospholipid or a nonionic surfactant. The phospholipid includes but is not limited to phosphatidylcholine, phosphatidylethanolamine, phosphatidylinositol, phosphatidylserine, phosphatidylglycerol, sphingomyelin and lecithin. Hydrogenated phospholipids may also be employed. The nonionic surfactant includes polyalkylene glycols (e.g. a polyethylene glycol with an average molecular weight of 1000~10000, preferably 4000~6000), polyoxyalkylene copolymers (e.g. a polyoxyethylene-polyoxypropylene copolymer with an average molecular weight of 1000~20000, preferably 6000~10000), hydrogenated castor oil polyoxyalkylene derivatives (e.g. hydrogenated castor oil polyoxyethylene (20) ether, do(40) ether, do(100) ether, etc.), and castor oil polyoxyalkylene derivatives (e.g. castor oil polyoxyethylene (20) ether, do(40) ether, do(100) ether, etc). These can be used each alone or in a combination of two or more species. The preferred emulsifying agent includes egg yolk phosphatidylcholine, egg yolk lecithin and soybean lecithin, among others. For practical purposes, egg yolk lecithin and soybean lecithin are preferred.

The level of said emulsifier in the inhalant of the invention should vary with the species of emulsifier and other components but may appropriately be 0.05~40 w/v %, preferably 0.1~20 w/v %.

The oil component-to-emulsifying agent (oil/emulsifier) ratio by weight may be 0.1~20, preferably 0.4~6.0, more preferably 0.8~1.2 (particularly 1).

The drug which can be used in the present invention is not particularly restricted but is preferably a drug which is more readily lipid-soluble than water-soluble. As such drugs, the so-called lipid-soluble drugs and water-insoluble drugs can be mentioned. Included among them are central nervous system drugs, peripheral nervous system drugs, sensory organ drugs, cardiovascular system drugs, respiratory system drugs, hormones, urogenital system drugs, drugs for anal diseases, vitamins, drugs for liver diseases, antigout drugs, enzymes, antidiabetics, immunosuppressants, cytoactivators, antitumoral drugs, radioactive drugs, antiallergic drugs, antibiotics, chemotherapeutic agents, biological drugs, and extracorporeal diagnostic agents.

More particularly, the following drugs can be mentioned by way of example.

1. Steroidal Drugs

Dexamethasone, prednisolone, betamethasone, beclomethasone propionate, triamcinolone, hydrocortisone, fludrocortisone and prasterone, salts thereof, and their lipid-soluble derivatives.

2. β-Adrenergic Agonists

Procaterol, orciprenaline, isoproterenol hydrochloride, pirbuterol, terbutaline, hexoprenaline, fenoterol hydrobromide, hexoprenaline sulfate, terbutaline sulfate, salbutamol sulfate, oxyprenaline sulfate, formoterol fumarate, isoprenaline hydrochloride, pirbuterol hydrochloride, procaterol hydrochloride, mabuterol hydrochloride, and tulobuterol, salts thereof, and their lipid-soluble derivatives.

3. Xanthine Derivatives

Diprophylline, proxyphylline, aminophylline and theophylline, salts thereof, and their lipid-soluble derivatives.

4. Antibiotics

Pentamidine isethionate, cefmenoxime, kanamycin, fradiomycin, erythromycin, josamycin, tetracycline, minocycline, chloramphenicol, streptomycin, midecamycin, amphotericin B, itraconazole and nystatin, salts thereof, and their lipid-soluble derivatives.

5. Others

Ipratropium bromide, methylephedrine hydrochloride, trimethoquinol hydrochloride, clenbuterol hydrochloride, oxitropium bromide, fultropium bromide, methoxyphenamine hydrochloride, chlorprenaline hydrochloride sodium cromoglycate.

The formulating level of the drug in the inhalant of the invention varies with the species of drug and other components but may suitably be 0.05~20 w/v %.

Furthermore, in the present invention, a co-emulsifier and/or an emulsion stabilizer can be formulated. The co-emulsifier and/or emulsion stabilizer includes straight-chain or branched-chain saturated or unsaturated fatty acids containing 6~22 carbon atoms, such as stearic acid, oleic acid, linoleic acid, palmitic acid, linolenic acid, myristic acid, etc. and salts thereof [e.g. alkali metal salts (sodium salts, potassium salts, etc.), alkaline earth metal salts (calcium salts etc.)]; primary or secondary aliphatic amines containing 2~22 carbon atoms, such as ethanolamine, propylamine, octylamine, stearylamine, oleylamine, etc.; basic amino acids such as lysine, histidine, ornithine, arginine, etc.; sterols such as cholesterol, cholestanol, etc.; and charged substances such as phosphatidic acid, ganglioside, stearylamine, etc. These may be used each alone or in a suitable combination of two or more species.

The formulating level of these substances depends on the objective to be achieved but may generally be not more than 2 w/v %, preferably not more than 1 w/v %.

In addition, pharmaceutically acceptable additives such as the antioxidant, preservative, isotonizing agent, buffer, stabilizer, etc. as well as adjuvants and nutrients may also be formulated. Specifically, benzoic acid, ascorbic acid, and tocopherol can be mentioned. These can be added generally in a suitable amount and need not be more than 10 w/v %.

The average particle diameter of the fat emulsion according to the present invention is 5~100 nm, preferably 5~70 nm, more preferably 10~50 nm. Also preferred is a fat emulsion with not less than 90% of fat emulsion particles falling within the particle size range of 5~100 nm.

While the fat emulsion particles of the inhalant of the present invention disperse in water, the water may for example be tap water, purified water, distilled water, water for injection, an electrolyte solution such as saline or a glucose solution.

The inhalant of the present invention can be freeze-dried to give a lyophilized composition. When it is to be provided in the form of such a lyophilizate, a suitable excipient is preferably formulated for the purpose of protecting freeze-dried fat emulsion particles, and/or the so-called freeze-dried cake. Such excipient includes saccharides, preferably disaccharides, specifically maltose, trehalose and sucrose. Particularly preferred is maltose.

The formulating level of said excipient in the inhalant of the invention varies with the species of excipient and other components but may suitably be 1~30 w/v %, preferably 3~20 w/v %.

The inhalant of the present invention can be manufactured by the known technology for the production of an ultrafine fat emulsion, i.e., Lipid Nanosphere [e.g. JP Kokai H2-203, JP Kokai H1-143826, JP Kokai H1-249716]. A typical process may comprise adding a drug, an emulsifier and other additive components in suitable amounts to a given quantity of an oil component, optionally heating the mixture for homogenization, adding a suitable amount of water and emulsifying the whole mixture with a conventional emulsifying machine such as the homomixer, homogenizer, ultrasonic homogenizer, Microfluidizer (tradename), Nanomizer (tradename), Ultimizer (tradename), or Manton-Gaulin high-pressure homogenizer until a predetermined particle size is attained. The emulsification can be carried out in two divided stages, namely preliminary emulsification and final emulsification.

The inhalant of the present invention can be filtration-sterilized by means of a 0.22 μm membrane filter.

The lyophilized inhalant of the present invention can be manufactured by freeze-drying said inhalant of the invention by the conventional procedure (e.g. PCT WO92/07552, JP Kokai H5-43450, JP Kokai H6-157294). For example, the inhalant of the invention is sterilized and distributed into vials. The vials are then subjected to preliminary freezing at about −40~−20° C. for about 2 hours, primary drying under reduced pressure at 0~10° C., and secondary freeze-drying under reduced pressure at about 15~25° C. The subsequent procedure generally comprises nitrogen gas purging and closing the vials to provide the lyophilized inhalant of the invention.

The inhalant of the invention can be administered to the human body through the nasal or oral cavity by generating aerosol particles of the inhalant with the aid of a device capable of generating an aerosol of an appropriate mist size according to the administration site (the upper respiratory tract, bronchioles, peripheral airways or alveolus) or the therapeutic objective (for the therapy of inflammation or for bronchodilation). The device for generating aerosol particles of the inhalant of the invention is not particularly restricted inasmuch as it is capable of producing aerosol particles 0.5~50 μm in diameter but is preferably a device adapted to generate an aerosol mist having a mass median aerodynamic diameter of 0.5~5 μm, particularly 1~2 μm. As specific examples of such device, there can be mentioned pressure nebulizers and ultrasonic nebulizers. Therefore, the present invention encompasses a nebulizer preparation comprising the inhalant of the invention. The inhalant of the invention may also be provided in the form of an inhalation aerosol preparation comprising the inhalant of the invention.

The lyophilized composition of the present invention can be applied to the human body by the airway route using an inhaler such as a nebulizer after it is reconstituted with an arbitrary suitable solution (a reconstitution medium) with or without agitation. The reconstitution medium which can be used in this manner includes tap water, purified water, distilled water, water for injection, an electrolyte solution inclusive of saline, a glucose solution, a standard infusion and drinking water, among others. The volume of the reconstitution medium is not particularly restricted but may suitably be 0.5~2 times as much as the volume of the pre-lyophilization solution or not more than 500 ml. Thus, the nebulizer preparation comprising a lyophilized form of the inhalant of the invention also falls within the scope of the present invention.

Furthermore, the lyophilized composition of the present invention can be micronized and directly inhaled in a finely divided form with the aid of a suitable inhaler such as a spinhaler or a diskhaler. Therefore, the present invention encompasses a powdery inhalant comprising the lyophilized composition of the invention.

With the aid of a suitable inhaler, the inhalant of the invention is capable of delivering the drug entrapped in its fat emulsion vesicles far enough to the pulmonary alveolus so that, depending on the intravascular migration efficiency of the fat emulsion particles, for instance, it can be indicated even when a systemic effect is desired.

BEST MODE FOR CARRYING OUT THE INVENTION

The following examples and test examples are intended to illustrate the present invention in further detail.

EXAMPLE 1

To 5 mg of cholesterylanthracene-9-carboxylate (CA), a fluorescent cholesterol derivative, as a mock drug, were added 500 mg of purified egg yolk lecithin, 500 mg of purified soybean oil, 9 mL of distilled water for injection and, further, 220 mg of glycerin J.P. and the mixture was sonicated with a probe type ultrasonic homogenizer (Branson Sonifier Model 185; the same applies hereinafter) under ice-water cooling for 60 minutes. The CA-containing fat emulsion thus obtained was light yellow and transparent. After the emulsion was diluted with distilled water for injection to make 10 mL, it was filtered through a 0.22 μm membrane filter to give a sterilized preparation, which was then filled in injection ampules, 2.0 mL/ampule, under nitrogen gas in a clean bench to prepare the inhalant of the invention. The average particle diameter of this inhalant fat emulsion as measured with a light scattering particle size analyzer (Otsuka Electronics, DLS-700; the same applies hereinafter) was 30.2 nm. Transmission electron microscopic observation revealed that these fat emulsion particles were uniform spherical nanospheres and the lipid bilayer structure like a liposome was not observed.

EXAMPLE 2

To 2 mg of amphotericin B (antifungal agent) were added 500 mg of soybean lecithin, 300 mg of cholesteryl oleate and 10 mL of distilled water for injection, and using a probe type ultrasonic homogenizer, the mixture was sonicated under ice-water cooling for 60 minutes. The amphotericin B-containing fat emulsion thus obtained was yellow and transparent. The emulsion was sterilized by filtration through a 0.22 μm membrane filter and filled in injection ampules, 2.0 mL per ampule, under nitrogen gas in a clean bench to give the inhalant of the invention. The average particle diameter of this inhalant fat emulsion as measured with a light scattering particle size analyzer was 40.2 nm. Transmission electron microscopic observation revealed that these fat emulsion particles were uniform spherical nanospheres and the lipid bilayer structure like a liposome was not observed.

EXAMPLE 3

To 100 mg of guaiazulene (antiinflammatory agent) were added 400 mg of egg yolk lecithin, 270 mg of triolein and 10 ml of saline, and using a probe type ultrasonic homogenizer, the mixture was sonicated under ice-water cooling for 40 minutes. The guaiazulene-containing fat emulsion thus obtained was blue and transparent. The emulsion was sterilized by filtration through a 0.22 μm membrane filter and filled in injection ampules, 2.0 mL per ampule, under nitrogen gas in a clean bench to give the inhalant of the invention. The average particle diameter of this inhalant fat emulsion as measured with a light scattering particle size analyzer was 22.1 nm. Transmission electron microscopic observation revealed that these fat emulsion particles were uniform spherical nanospheres and the lipid bilayer structure like a liposome was not observed.

EXAMPLE 4

To 1 mg of beclomethasone propionate (a steroid) were added 400 mg of egg yolk lecithin, 270 mg of medium-chain fatty acid triglyceride and 10 mL of distilled water for injection, and using a probe-type ultrasonic homogenizer, the mixture was sonicated under ice-water cooling for 50 minutes. The beclomethasone propionate-containing fat emulsion thus obtained was light yellow and transparent. The emulsion was sterilized by filtration through a 0.22 μm membrane filter and filled in injection ampules, 2.0 mL per ampule, under nitrogen gas in a clean bench to give the inhalant of the invention. The average particle diameter of this inhalant fat emulsion as measured with a light scattering particle size analyzer was 35.2 nm. Transmission electron microscopic observation revealed that these fat emulsion particles were uniform spherical nanospheres and the lipid bilayer structure like a liposome was not observed.

EXAMPLE 5

To 50 mg of cyclosporin A (immunosuppressant) was added 500 mg of purified egg yolk lecithin, 500 mg of purified soybean oil, 9 mL of distilled water for injection, and further 220 mg of glycerin JP, and using a probe-type ultrasonic homogenizer, the mixture was sonicated under ice-water cooling for 60 minutes. The cyclosporin A-containing fat emulsion thus obtained was light yellow and transparent. This emulsion was diluted with distilled water for injection to make 10 mL and filtered through a 0.22 μm membrane filter and the sterile filtrate was filled into injection ampules, 2.0 mL per ampule, under nitrogen gas in a clean bench to give an inhalant of the invention. The average particle diameter of this inhalant fat emulsion as measured with a light scattering particle size analyzer was 40.2 nm. Transmission electron microscopic observation revealed that these fat emulsion particles were uniform spherical nanospheres and no lipid bilayer structure like a liposome was observed.

EXAMPLE 6

To 1 mg of dexamethasone palmitate (a steroid) were added 400 mg of soybean lecithin, 400 mg of triolein and 10 mL of distilled water for injection, and using a probe-type ultrasonic homogenizer, the mixture was sonicated under ice-water cooling for 50 minutes. The dexamethasone palmitate-containing fat emulsion thus obtained was light yellow and transparent. The emulsion was sterilized by filtration through a 0.22 μm membrane filter and filled in injection ampules, 2.0 mL per ampule, under nitrogen gas in a clean bench to give the inhalant of the invention. The average particle diameter of this inhalant fat emulsion as measured with a light scattering particle size analyzer was 29.6 nm. Transmission electron microscopic observation revealed that these fat emulsion particles were uniform spherical nanospheres and the lipid bilayer structure like a liposome was not observed.

EXAMPLE 7

To 1 g of diphenhydramine (antihistaminic) were added 40 g of soybean lecithin, 40 g of triolein and 1 mL of 10% maltose, and the mixture was emulsified with a Manton-Gaulin homogenizer. The diphenhydramine-containing fat emulsion thus obtained was light-yellowish white~yellowish white and transparent. The average particle diameter of this fat emulsion as determined with a light scattering particle size analyzer was 38.9 nm. This emulsion was sterilized by filtration through a 0.22 μm membrane filter and filled in injection vials, 2.0 ml per vial, in a clean bench, followed by freeze-drying to provide a lyophilized version of the inhalant of the invention. This lyophilized inhalant was reconstituted with distilled water for injection and the average particle diameter of the fat emulsion was determined with a light scattering particle size analyzer. The result was 40.1 nm. Transmission electron microscopic observation revealed that the fat emulsion comprised uniform spherical nanospheres and no lipid bilayer structure like a liposome was observed.

EXAMPLE 8

To 1 g of prednisolone (a steroid) were added 60 g of soybean lecithin, 50 g of trilinolein and 1 L of 10% maltose, and the mixture was emulsified with a Manton-Gaulin homogenizer. The prednisolone-containing fat emulsion thus obtained was white and transparent. The average particle diameter of this fat emulsion as determined with a light scattering particle size analyzer was 37.5 nm. This emulsion was sterilized by filtration through a 0.22 μm membrane filter and filled in injection vials, 2.0 ml per vial, in a clean bench, followed by freeze-drying to provide a lyophilized version of the inhalant of the invention. This lyophilized inhalant was reconstituted with distilled water for injection and the average particle diameter of the fat emulsion was determined with a light scattering particle size analyzer. The result was 33.3 nm. Transmission electron microscopic observation revealed that the fat emulsion comprised uniform spherical nanospheres and no lipid bilayer structure like a liposome was observed.

EXAMPLE 9

To 1 g of amphotericin B (antifungal agent) were added 50 g of soybean lecithin, 50 g of triolein and 1 L of 10% trehalose, and the mixture was homogenized with a microfluidizer-type homogenizer (M110-E/H). The amphotericin B-containing fat emulsion thus obtained was yellow and transparent. The average particle diameter of this fat emulsion as determined with a light scattering particle size analyzer was 32.9 nm. This emulsion was sterilized by filtration through a 0.22 μm membrane filter and filled in injection vials, 2.0 ml per vial, in a clean bench, followed by freeze-drying to provide a lyophilized version of the inhalant of the invention. This lyophilized inhalant was reconstituted with distilled water for injection and the average particle diameter of the fat emulsion was determined with a light scattering particle size analyzer. The result was 35.5 nm. Transmission electron microscopic observation revealed that this fat emulsion comprised uniform spherical nanospheres and no lipid bilayer structure like a liposome was observed.

EXAMPLE 10

The lyophilized inhalant of the invention (125 g) as obtained in Example 9 was micronized to a particle diameter of 0.5~4 μm and filled in hard capsule shells, 0.25 g per capsule. By this procedure, 500 capsules each containing 1.25 mg of amphotericin B were obtained. The capsule was pierceable with a pulverizer-powder inhaler (JP Koho S63-6024) whereby the contents were made inhalable.

EXAMPLE 11

To 0.2 g of tulobuterol (β2 adrenergic agonist) were added 50 g of egg yolk lecithin, 50 g of rapeseed oil and 1 L of 10% sucrose, and the mixture was emulsified with a microfluidizer type homogenizer (M110-E/H). The tulobuterol-containing fat emulsion thus obtained was off-white and transparent. The average particle diameter of this fat emulsion as determined with a light scattering particle diameter analyzer was 36.6 nm. This emulsion was sterilized by filtration through a 0.22 um membrane filter and filled in injection vials, 2.0 mL per vial, in a clean bench, followed by freeze-drying to give a lyophilized version of the inhalant of the invention. This lyophilized inhalant was reconstituted with distilled water for injection and the average particle diameter of the fat emulsion was determined with a light scattering particle size analyzer. The result was 38.7 nm. Transmission electron microscopic observation revealed that this fat emulsion comprised uniform spherical nanospheres and no lipid bilayer structure like a liposome was observed.

EXAMPLE 12

The lyophilized inhalant of the invention (250 g) as obtained in Example 11 was micronized to a particle diameter of 0.5~4 μm and filled in hard capsule shells, 0.5 g per capsule. By this procedure, 1000 capsules each containing 0.5 mg of tulobuterol were obtained. The capsule was pierceable with a pulverizer-powder inhaler (JP Koho S63-6024) whereby the contents were made inhalable.

Test Example 1
Determination of Mass Median Aerodynamic Diameter (MMAD) and Its Distribution (I)

The CA-containing inhalant of the invention as prepared in Example 1 was used as a test sample and a known fat emulsion having an average particle diameter of 0.2 μm in which CA had been entrapped was used as a control sample. This control sample was prepared by adding 9 mL of distilled water for injection to a mixture of 5 mg of CA, 100 mg of purified soybean oil and 12 mg of purified egg yolk lecithin, further adding 220 mg of glycerin JP, homogenizing the whole mixture with a probe type ultrasonic homogenizer under ice-water cooling, and making up the emulsion to 10 mL with distilled water for injection.

The measurement of mass median aerodynamic diameter and its distribution was carried out with Anderson's Cascade Impactor (listed in USP) which classifies particles into multiple stages by utilizing differences in inertia in the aspiration of an aerosol at a constant speed.

In the experiment, a nebulizer body [Medical Device Approval No. (55B) 1329; the same applies hereinafter] was attached to a Nissho model compressor [Medical Device Approval No. (55B) 1270; the same applies hereinafter] in the first place and each sample was sprayed at a flow rate of 6 L/min. for 80 minutes to generate a mist of aerosol particles. The aerosol particles thus produced were aspirated with a vacuum pump at a flow rate of 28.3 L/min. and classified into multiple stages. The aerosol particles captured in each stage were washed with methanol and recovered, and its fluorescence intensity was measured to estimate the amount of the drug. The results are shown in FIG. 1.

It can be seen from FIG. 1 that, compared with the control sample, the test sample gave larger drug amounts in the stages from 0 to 2.1 $\mu$m, with a significant difference at p<0.01. In particular, whereas the control sample was scarcely captured in the stages up to 2.1 $\mu$m, about 70% of the total amount of the drug recovered was found in these stages. This is probably because particles of small mass median aerodynamic diameter could be produced by reducing the particle diameter of the fat emulsion. In the stages >2.1 $\mu$m~$\leqq$9 $\mu$m, no significant difference was found at the p<0.05 level between the two groups. It was also confirmed that the total amount of the drug recovered in all the stages was about 3-fold greater in favor of the test sample as compared with the control sample.

The mass median aerodynamic diameter is a factor of great importance for the drug to reach and get deposited at the target site. In humans, the mass median aerodynamic diameter of particles entering the airway is considered to be 1~10 $\mu$m and it is acknowledged that aerosol particles within the diameter range of 2~5 $\mu$m, in particular, are optimal for the drug reaching and getting deposited in the airway (the bronchus to the terminal bronchiole) and that the particles capable of reaching the alveolus located deeper is 1~2 $\mu$m in diameter (JP Forum Vol. 4, No. 1, 1995). As can be readily inferred from the results of this Test Example 1 in which the test sample was found to be significantly rich in the fraction of aerosol particles not greater than 2.1 $\mu$m in diameter as compared with the control sample, the inhalant of the invention easily generates aerosol particles 1~2 $\mu$m in diameter which can hardly be obtained with the conventional fat emulsion. Thus, it can be suggested that the delivery of the drug deep into the alveolus which could not be achieved with the conventional fat emulsion can now be easily accomplished in accordance with present invention.

Test Example 2

Determination of Mass Median Aerodynamic Diameter (MMAD) and Its Distribution (II)

Using the CA-containing inhalant according to Example 1 of the invention as a test sample, the mass median aerodynamic diameter and its distribution were measured by varying the nebulizer spray condition. Thus, spraying was carried out with the rubber plug on the nebulizer body kept closed (condition-1; the same as the test sample of test Example 1) or with the rubber plug kept open (condition-2). It is generally acknowledged that finer aerosol particles are obtained under condition-1 while coarser particles are obtained under condition-2. As in Test Example 1, the measurements were carried out using Anderson's Cascade Impactor, Nissho model compressor, and nebulizer body, and the compressor and vacuum suction air flow rates were also the same as in Test Example 1. The aerosol particles captured in each stage were washed with methanol and recovered and the amount of the drug was estimated by measuring the intensity of fluorescence. The results are shown in FIG. 2.

It will be apparent from FIG. 2 that the test sample yielded fine aerosol particles with a peak distribution at 1.1~2.1 $\mu$m under condition-1 and relatively coarse aerosol particles with a peak at 2.1~3.3 $\mu$m under condition-2. As mentioned above, the mass median aerodynamic diameter is a factor of great importance for the drug to reach and get deposited at the target site. In humans, it is acknowledged that aerosol particles within the range of 2~5 $\mu$m, in particular, are optimal for the drug to reach and settle in the airway (the bronchus to the terminal bronchiole) and that the particles capable of reaching the alveolus lying deeper is 1~2 $\mu$m in diameter. Meanwhile, some drugs have the bronchus as the target site, while others are to be absorbed from the pulmonary alveolus to produce a systemic effect, and the optimum mass median aerodynamic diameter of aerosol particles should be determined according to the mechanism of action of each drug. This experiment has demonstrated that the particle diameter of aerosol particles of the test sample could be adjusted by selective use of spray condition-1 or condition-2, indicating clearly that the invention is applicable to both a drug acting on the bronchus and a drug to be administered for systemic effects.

Test Example 3

An Experiment on the Concentration of a Solution in Nebulizer Spraying

The CA-containing inhalant of the invention was used as a test sample and the same CA-containing 0.2 $\mu$m (dia.) fat emulsion as used in Test Example 1 was used as control sample-1. As control sample-2, saline was used.

Sampling was made on the residual solution in the nebulizer after 80 minutes' spraying with the nebulizer body attached to the Nissho model compressor at a flow rate of 6 L/min. The residual concentrations of the test sample and control sample-1 were determined by fluorometric assay of CA, while the residual concentration of control sample-2 was determined by measuring the concentration of sodium by the electrode method. The results are shown in FIG. 3.

It will be apparent from FIG. 3 that the test sample showed substantially the same concentration gain as control sample-2, while control sample-1 showed a significantly greater concentration gain. The finding of concentration gains for all the samples is suggestive of the influence of evaporation of water. On the other hand, the finding of a significantly large concentration gain of control sample-1 suggests that aerosol particles of water alone, not containing fat emulsion particles with a diameter of 0.2 $\mu$m, are generated and scattered. This can be understood if only from the finding in Test Example 1 that aerosol particles not greater than 2.1 $\mu$m in diameter scarcely contained the drug. Thus, it appears that when an inhalant composed of a fat emulsion with a particle diameter of 0.2 $\mu$m is sprayed with a nebulizer, aerosol particles not greater than 2.1 $\mu$m in diameter are produced but the emulsion particles with a diameter of 0.2 $\mu$m does not account for any large fraction thereof. On the other hand, the test sample showed substantially the same concentration gain as control sample-2, suggesting that aerosol particles composed of water alone are scarcely produced.

Test Example 4

Filter-sterilization Test

The CA-containing inhalant according to Example 1 of the present invention was used as a test sample and the same 0.2 $\mu$m (dia.) fat emulsion in which CA had been entrapped as used in Test Example 1 was used as a control sample.

In the experiment performed using a pressure filtration apparatus and a 0.22 μm (pore) membrane filter (cellulose acetate +nitrocellulose; Millipore, MF Millipore), 10 mL of each sample was filtered and the quantity of the filtrate and the percent recovery of the drug were determined. The results are shown in Table 1.

TABLE 1

|  | Filtrate (mL) | Drug recovery (%) |
|---|---|---|
| Test sample | 9.9 ± 0.2 | 100 ± 1.3 |
| Control sample | 1.3 ± 0.1 | 12 ± 2.3 |

It will be apparent from Table 1 that whereas the control sample could hardly be filtration-sterilized, the test sample could be effectively filtration-sterilized.

Test Example 5
Transpulmonary Administration Experiment in Rabbits (−1)
Using 6 male 9-week-old rabbits (Kbs: JW), the trachea was exposed under anesthesia and connected to a Y-cannula and the animal was placed on supportive respiration using a respirator. Under supportive respiration, the inhalant according to Example 5 of the present invention as a test sample and the same 0.2 μm fat emulsion as used in test Example 1 in which cyclosporin A had been entrapped as a control sample were administered each in a dose of 5 mg/kg by 30 (ca) minutes' spraying using a Nissho model compressor and a nebulizer body connected thereto. After completion of inhalation, the cannula was disconnected and the cannulation wound was sutured. Then, the blood was drawn from the auricular vein at timed intervals and the time course of plasma cyclosporin A concentration was monitored by fluorescence polarization immunoassay (FPIA). The results are shown in FIG. 4.

It will be apparent from FIG. 4 that the plasma cyclosporin A concentration was consistently higher in the test sample administration group than in the control sample administration group, with a difference of about 3-fold in the area under the plasma concentration-time curve (AUC). Thus, although the translocation of an inhaled drug into the systemic circulation depends upon arrival of the drug at the alveolus, the control 0.2 μm (dia.) fat emulsion is hardly able to deliver the drug to the alveolus. In the case of the inhalant of the invention, as can be seen if only from the result of Test Example 1, the drug is entrapped in aerosol vesicles capable of reaching the alveolus. It is obvious from the result of this transpulmonary administration experiment in rabbits that the inhalant of the invention as the test sample is outstanding in the ability to reach the alveolus.

Test Example 6

Transpulmonary Administration Experiment in Rabbits (−2)

Using 6 male 9-week-old rabbits (Kbs: JW), the trachea was exposed under anesthesia and connected to a Y-cannula and the animal was placed on supportive respiration using a respirator. Under supportive respiration, the inhalant according to Example 5 of the invention as a test sample and an inhalant comprising cyclosporin A solubilized with Tween-80 as a control sample were administered each in a dose of 1 mg/kg by 30 (ca) minutes' spraying using a Nissho model compressor and a nebulizer body attached thereto. After completion of inhalation, the cannula was disconnected and the cannulation wound was sutured. Then, the blood was drawn from the auricular vein at timed intervals and the time course of plasma cyclosporin A concentration was monitored by fluorescence polarization immunoassay (FPIA). The results are shown in FIG. 5.

It can be seen from FIG. 5 that the AUC showed no difference at the $p<0.05$ level between the test sample administration group and the control sample administration group. The two groups were almost comparable in the time course of plasma concentration up to 2 hours but the concentration in the test sample administration group after 3 hours declined slightly as compared with the control sample administration group. Thus, the inhalant of the invention as the test sample was superior to the surfactant-solubilized control inhalant in the slow and prolonged release characteristics in the plasma.

Test Example 7

Influence of the Solubilization-effective Surfactant Concentration on Sprayability The samples of CA, guaiazulene and dexamethasone palpitate each solubilized with HCO-60, propylene glycol, sodium lauryl sulfate, Tween-80 or Triton X100 were compared with the inhalants according to Examples 1, 3 and 6 of the present invention in nebulizer sprayability. The results are shown in Table 2.

TABLE 2

| | CA | Guaiazulene | Dexamethasone palmitate |
|---|---|---|---|
| HCO-60 | Infeasible | Infeasible | Infeasible |
| Propylene glycol | Infeasible | Infeasible | Infeasible |
| Sodium lauryl sulfate | Infeasible | Infeasible | Infeasible |
| Tween-80 | Infeasible | Infeasible | Infeasible |
| Triton X100 | Infeasible | Infeasible | Infeasible |
| Inhalant of invention | Example 1 Feasible | Example 3 Feasible | Example 6 Feasible |

It will be apparent from Table 2 that all the solutions prepared with a surfactant or a solubilizer could hardly be sprayed because of the foam produced in the nebulizer body.

Test Example 8

Measurement of Kinetic Viscosity

The CA-containing inhalant of the invention as prepared in Example 1 was used as a test sample and the same 0.2 μm fat emulsion as used in Test Example 1 in which CA had been entrapped was used as a control sample.

The kinetic viscosities of the test sample and control sample were measured with a capillary viscometer (n=10). Since the viscosities to be measured were comparatively close to the viscosity of water, water was used as the reference solution. The kinetic viscosity of water is 1.0038 $mm^2/s$ at 20° C. The results are shown in Table 3.

TABLE 3

| | Kinetic viscosity ($mm^2/s$) |
|---|---|
| Test sample | 1.0323 ± 0.0021 |
| Control sample | 1.4985 ± 0.0038 |

It will be apparent from Table 3 that the kinetic viscosity of the test sample is lower than that of the control sample. Therefore, the inhalant of the present invention is capable of yielding finer aerosol particles easily with the aid of a nebulizer or the like.

EFFECTS OF INVENTION

The following, among others, may be mentioned as effects of the present invention.

(1) The inhalant of the invention is low in viscosity and does not substantially produce a foam in the nebulizer or the like; it yields a mist of aerosol particles easily with the aid of a suitable inhaler such as a nebulizer.
(2) With the aid of a suitable inhaler, the inhalant of the invention readily yields a mist of aerosol particles fine enough to reach the alveolus; the inhalant is well amenable to size control of the aerosol particles.
(3) The inhalant of the invention can be used in expectation of a systemic effect by the pulmonary route. Therefore, it is not limited to topical application to the respiratory tract, bronchus, alveolus or the like. Moreover, the sustained action and improved bioavailability can be expected.
(4) It can be sterilized by filtration using a 0.22 μm membrane filter. Therefore, the invention is useful for heat-labile drugs which cannot be autoclaved for sterilization.

Figure 1:
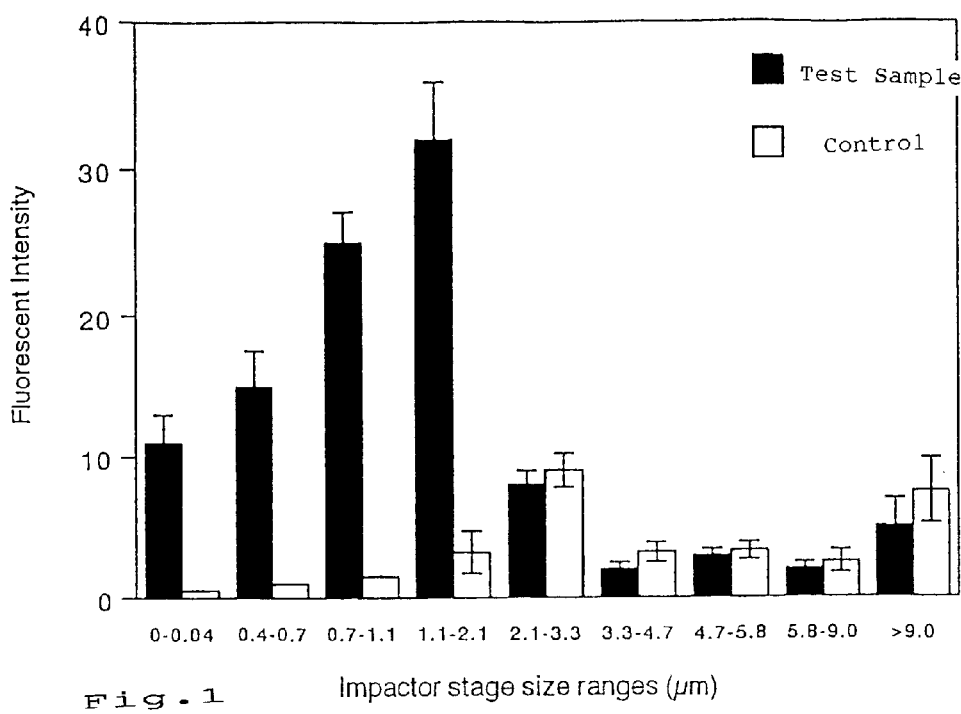
FIG. 1 represents the amount of the drug in each aerosol particle size stage. The abscissa represents the impactor stage size ranges (μm) and the ordinate represents the fluorescent intensity. The solid bar represents the inhalant of the invention and the open bar represents the control.
Figure 2:
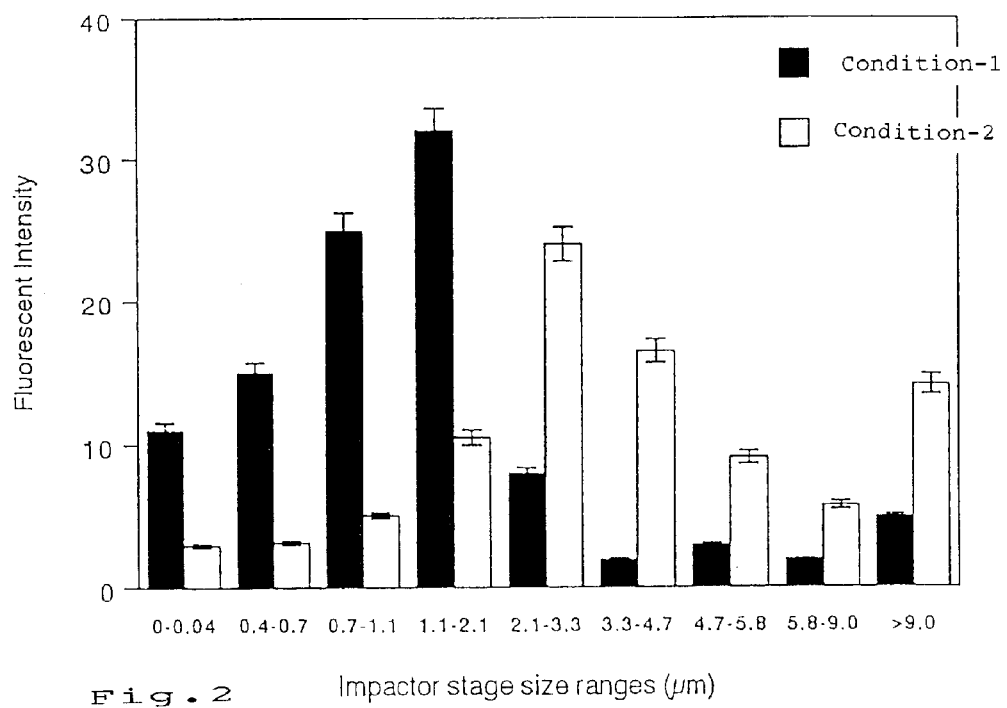
FIG. 2 shows the amount of the drug in each aerosol particle size stage. The abscissa represents the impactor stage size ranges (μm) and the ordinate represents the fluorescent intensity. The solid bar represents condition-1 and the open bar represents condition-2.
Figure 3:
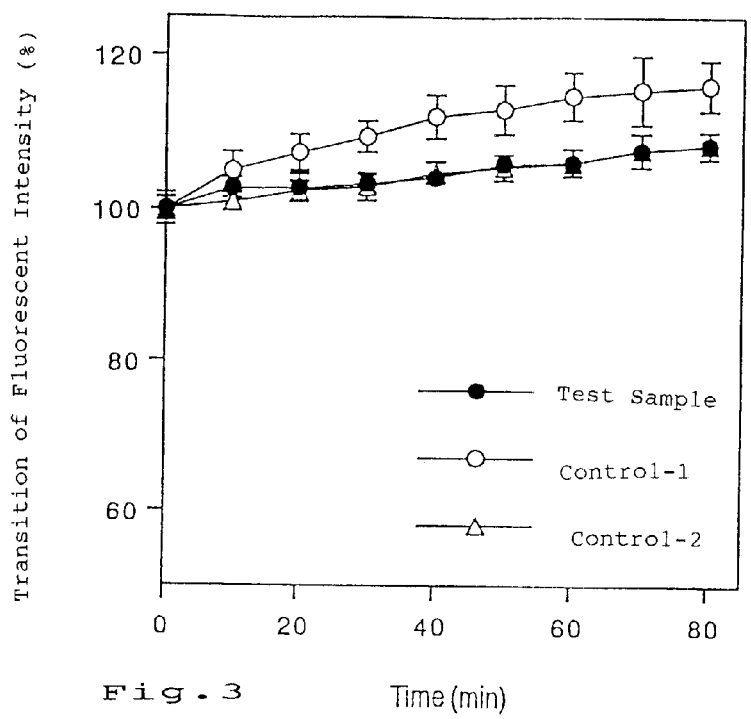
FIG. 3 shows the time course of concentration of the spray solution. The abscissa represents time (min.) and the ordinate represents the fluorescent intensity. -●- represents the test sample (the inhalant of the invention); -○- represents control sample-1; and -△- represents control sample-2 (physiological saline).
Figure 4:
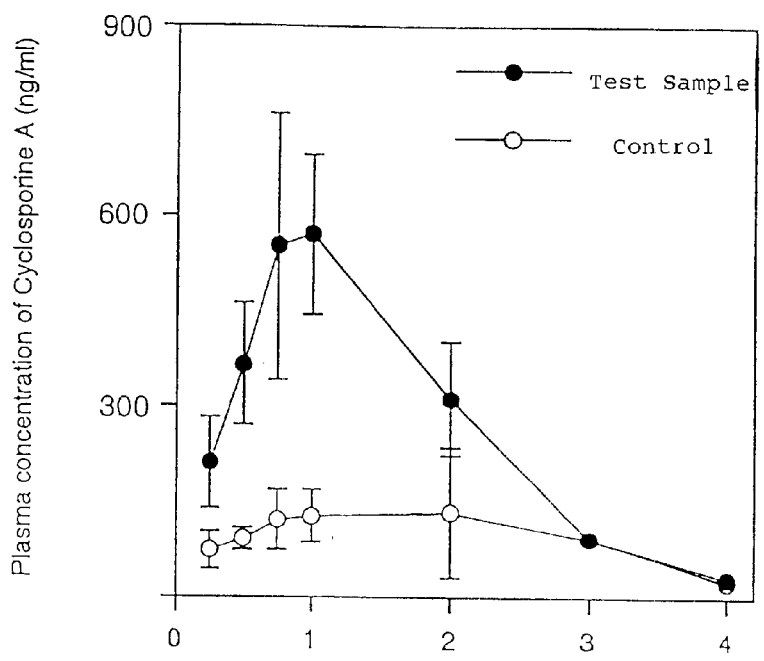
FIG. 4 shows the results of a transpulmonary administration experiment in rabbits. The abscissa represents time (hr.) and the ordinate represents the plasma concentration of cyclosporin A (ng/ml). -●- represents the inhalant of the invention and -○- represents the control inhalant.
Figure 5:
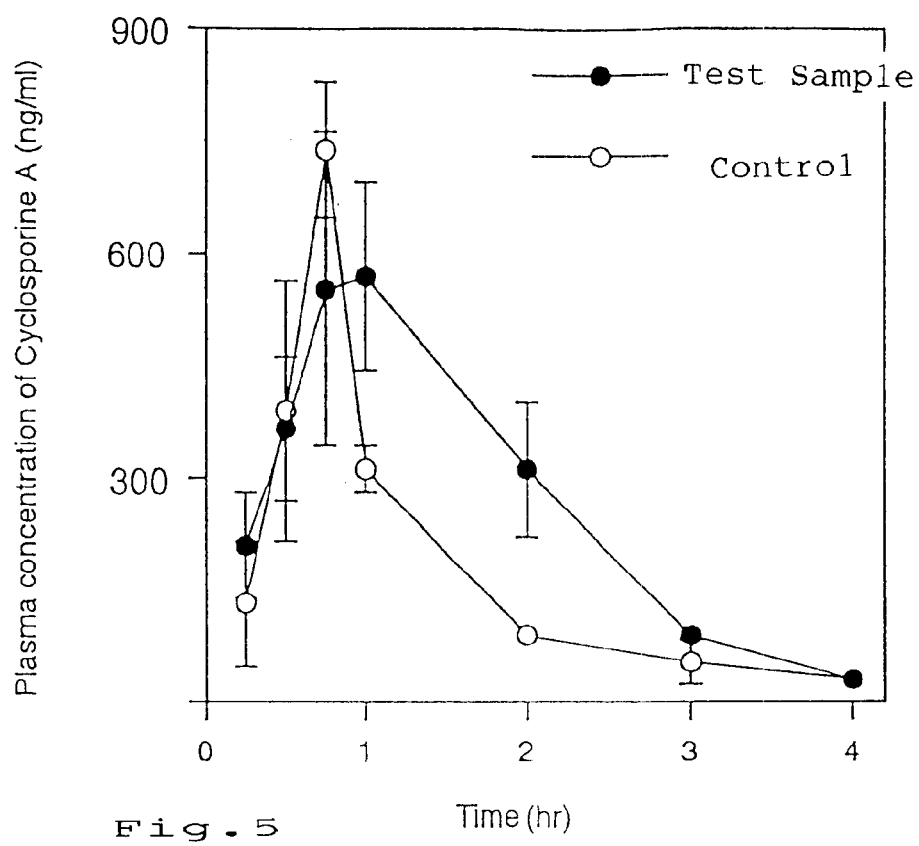
FIG. 5 shows the results of a transpulmonary administration experiment in rabbits. The abscissa represents time (hr.) and the ordinate represents the plasma concentration of cyclosporin A (ng/ml). -●- represents the inhalant of the invention and -○- represents the control inhalant.

What is claimed is:
1. A medical fat emulsion for inhalational administration to an individual, or a lyophilized composition thereof, wherein said emulsion is an o/w fat emulsion comprising an aqueous dispersion of uniform and spherical ultrafine fat emulsion particles essentially composed of an oil component, a phospholipid and a sparingly water-soluble medical drug, wherein the average particle diameter of said fat emulsion particles is within a range of 5–100 nm.

2. The fat emulsion or lyophilized composition thereof as claimed in claim 1 wherein the proportion of said oil component of the fat emulsion lies within the range of 0.1~30 w/v % and the proportion of said emulsifying agent lies within the range of 0.05~40 w/v %.

3. The fat emulsion or lyophilized composition thereof as claimed in claim 1 wherein the weight ratio of said oil component to said emulsifying agent (oil/emulsifier ratio) lies within the range of 0.1~20.

4. The fat emulsion or lyophilized composition thereof as claimed to claim 1 wherein the oil component is a vegetable oil or a glyceride and the emulsifying agent is a phospholipid or a nonionic surfactant.

5. The fat emulsion or lyophilized composition thereof as claimed in claim 4 wherein the vegetable oil is soybean oil and the phospholipid is egg yolk lecithin.

6. The fat emulsion or lyophilized composition thereof as claimed in claim 1 further comprising a saccharide.

7. A lyophilized composition obtainable by freeze-drying the inhalant fat emulsion of claim 6 wherein the amount of said saccharide in the fat emulsion is 1~30 w/v %.

8. A lyophilized composition of the inhalant fat emulsion of claim 6 wherein the saccharide is a disaccharide.

9. The inhalant fat emulsion or lyophilized composition thereof as claimed in claim 7 further comprising a fatty acid and/or cholesterol.

10. A nebulizer preparation comprising the inhalant fat emulsion or lyophilized composition thereof claimed in claim 1.

11. A powdery inhalant comprising a lyophilized composition of the inhalant fat emulsion claimed in claim 1.

12. A method of administering a medical fat emulsion or a lyophilized composition thereof to an individual, wherein said fat emulsion is an o/w fat emulsion comprising an aqueous dispersion of uniform and spherical ultrafine fat emulsion particles, each composed essentially of an oil component, an emulsifying agent and a drug, wherein the average particle diameter of said fat emulsion particles is within the range of 5–100 nm, wherein said emulsion or said composition is administered by inhalation by said individual.

* * * * *